United States Patent [19]
Bauer et al.

[11] Patent Number: 6,107,055
[45] Date of Patent: Aug. 22, 2000

[54] METHOD AND DEVICE FOR CARRYING OUT BIOCHEMICAL REACTIONS

[75] Inventors: Hermann Bauer, Lauf; Horst Menzler, Bernfried; Gerd Kleinhammer, Tutzing; Hans Schels, Munich; Peter Bendzko, Berlin; Ute Fink; Bernd Maciej, both of Nürnberg, all of Germany

[73] Assignee: Roche Diagnostics GmbH, Mannheim, Germany

[21] Appl. No.: 09/124,985

[22] Filed: Jul. 30, 1998

[30] Foreign Application Priority Data

Jul. 31, 1997 [DE] Germany ............... 197 32 935

[51] Int. Cl.⁷ ............... C12P 21/06; C12P 1/00
[52] U.S. Cl. ............... 435/68.1; 435/41; 435/286.5; 435/297.1; 435/297.2; 210/321.7; 210/321.75
[58] Field of Search ............... 435/285.5, 297.1, 435/297.2, 41, 68.1; 210/321.72, 321.75

[56] References Cited

U.S. PATENT DOCUMENTS

| | | | |
|---|---|---|---|
| 5,135,853 | 8/1992 | Dziewulski et al. | 435/41 |
| 5,434,079 | 7/1995 | Mozayeni | 435/297.2 |
| 5,478,730 | 12/1995 | Alakhov et al. | 435/68.1 |

FOREIGN PATENT DOCUMENTS

| | | |
|---|---|---|
| 0 638 641 | 7/1994 | European Pat. Off. . |
| 39 14956 | 11/1990 | Germany . |
| 84/01959 | 5/1984 | WIPO . |
| 86/02379 | 4/1986 | WIPO . |
| 93/03135 | 2/1993 | WIPO . |
| 94/18341 | 8/1994 | WIPO . |
| 94/20603 | 9/1994 | WIPO . |

*Primary Examiner*—Herbert J. Lilling
*Attorney, Agent, or Firm*—Arent Fox Kintner Plotkin & Kahn, PLLC

[57] ABSTRACT

Method and apparatus for carrying out biochemical reactions in particular for cell-free polypeptide biosynthesis. A bioreactor has, within a housing, a reaction chamber containing a producing system as well as a supply chamber separated from the reaction chamber by means of a semi-permeable membrane and containing a liquid serving as supply medium for the producing system. The supply chamber is subdivided within the bioreactor into a first partial chamber and a second partial chamber which are each connected to the reaction chamber via a semi-permeable supply membrane and which are connected to each other by means of a connection conduit. During the biochemical reaction, liquid is circulated from the first partial chamber of the supply chamber through the reaction chamber and into the second partial chamber of the supply chamber in such a fashion that, during each passage of liquid out of the first partial chamber into the reaction chamber, liquid simultaneously passes from the reaction chamber into the second partial chamber and liquid flows out of the second partial chamber via the connection conduit back into the first partial chamber.

11 Claims, 3 Drawing Sheets

METHOD AND DEVICE FOR CARRYING OUT BIOCHEMICAL REACTIONS

The invention concerns a method and a device for carrying out biochemical reactions in particular for cell-free biosynthesis of proteins or other polypeptides.

In biotechnological applications, biochemical reactions are usually effected in bioreactors. Examples of such biochemical reactions are enzyme reactions by which a substrate is transformed from an initial state into a final state by catalytic action of an enzyme and the biosynthesis of naturally occurring substances, for example peptide hormones, antibiotics and, most recently of particular importance, human proteins.

The totality of biochemically active components in these reactions are generally referred to as the "producing system". The producing system almost invariably contains extremely expensive components which, however, are not used up or only used up to a small extent during the reaction. For this reason, they are immobilized within the bioreactor in a reaction chamber. The invention is directed to a method, wherein the reaction chamber in the bioreactor is separated from a supply chamber by means of a semipermeable membrane.

A method for cell-free biosynthesis of polypeptides is e.g. described in U.S. Pat. No. 5,478,730. The producing system contains a source of messanger-RNA (mRNA) which encodes the polypeptide. The cell-free synthesis system further contains ribosomes, tRNA, amino acids, ATP and GTP. Translation of the mRNA with the assistance of the tRNA leads to the production of the polypeptide, wherein simultaneously products of low molecular weight result. The reaction chamber containing the producing system is separated from a supply chamber by means of a semi-permeable barrier. The supply chamber contains a liquid acting as supply medium for the producing system and containing ATP, GTP and amino acids. These components are introduced to the producing system to replace consumption during the biological reaction. They can diffuse through the semi-permeable barrier since their molecular weights are below its molecular weight (MW) cutoff. Simultaneously products of the biochemical reaction and other substances whose molecular weight is less than the MW-cutoff of the barrier diffuse out of the reaction chamber into the supply chamber.

U.S. Pat. No. 5,478,730 recommends using semi-permeable barriers, particularly in the form of hollow fiber membranes (subsequently referred to as "capillary membranes"). The MW-cutoff of the semi-permeable membrane is chosen in such a fashion that the low molecular reaction components, which are necessary for maintenance of the biochemical reaction, can pass into and the relatively low molecular products can be removed from the reaction chamber. In contrast thereto, the mRNA and other particularly valuable high molecular components of the producing system are kept within the reaction chamber. The MW-cutoff advantageously is less than 100,000 Dalton, and preferably below 50,000 Dalton. It should, however, be more than approximately 1,000 to 5,000 Dalton.

The cited US patent contains a large amount of additional description concerning suitable compositions for the producing system and the supply medium as well as how to carry out the biosynthesis. In this respect the present invention refers to the prior art as particularly described by U.S. Pat. No. 5,478,730 and the literature and references cited therein, the disclosure of which are hereby incorporated by reference.

If the invention is used for biochemical reactions other than polypeptide synthesis, a producing system adapted to the appropriate application is utilized. Further description thereof can also be obtained from the relevant literature references. A producing system can, in principle, be any system which is capable of facilitating or accelerating the transformation or synthesis of desired compounds using biochemical means. In addition to the systems mentioned, this refers in particular to enzymes and enzyme complexes in combination with the auxiliary substances normally used in these types of processes.

Since the mRNA needed for biosynthesis of polypeptides is only available at acceptable cost in very small quantities and since the produced product amounts are also very small, such reactions are often carried out in very small bioreactors. The invention is particularly directed towards micro-membrane-reactors which normally have a reaction chamber volume of approximately 1 ml (in any event less than 10 ml). These are throw-away products. Therefore the economical manufacture of such micro-membrane-reactors is of particular importance.

It is an object of the invention to provide a method and a device with which biochemical reactions can be carried out with high effectiveness and in an economical fashion.

This purpose is achieved by a method for carrying out biochemical reactions, in particular for cell-free polypeptide biosynthesis, using a bioreactor having, within a housing, a reaction chamber containing a producing system and a supply chamber separated from the reaction chamber via a semi-permeable membrane and containing a liquid acting as a supply medium for the producing system, wherein the supply chamber within the bioreactor is divided into a first partial chamber and a second partial chamber each of which is connected via a semi-permeable membrane (designated as supply membrane) to the reaction chamber and which are connected to each other by means of a connecting conduit, via which, during the biochemical reaction, liquid is circulated from the first partial chamber of the supply chamber through the reaction chamber into the second partial chamber of the supply chamber in such a fashion that, during passage of liquid out of the first partial chamber into the reaction chamber, liquid simultaneously flows from the reaction chamber into the second partial chamber and liquid flows out of the second partial chamber via the connection conduit back into the first partial chamber.

In a device in accordance with the invention for carrying out the method, each partial chamber of the supply chamber in the reactor has a connection opening for the connection conduit, wherein a pump is disposed in the connection conduit for circulating the liquid. Such a device can be designated as a bioreactor system, wherein the pump and the connection conduit can either be separate from, but functionally adapted to the bioreactor module of the system or can be integrated into the bioreactor housing.

Conventional bioreactors normally have one single supply chamber within the reactor housing. In accordance with the invention, the supply chamber within the bioreactor comprises two partial chambers which are connected for liquid transmission by means of a connection conduit containing a pump but which are otherwise separated from another. Liquid can be pumped from one partial chamber into the other partial chamber by the pump via the connection conduit. Each of the partial chambers is connected to the reaction chamber by means of a supply membrane. When the pump is operated, pressure is generated in the upstream partial chamber. In this manner, liquid flow is initiated through the supply membrane into the reaction chamber. The resulting pressure in the reaction chamber leads to the simultaneous flow of liquid out of the reaction chamber into the second partial chamber. Liquid is pumped therefrom via the connecting conduit and the pump to effect circulation. If, in accordance with a preferred embodiment, the liquid volumes in the partial chambers of the circulation system (reaction chamber, both partial chambers of the supply chamber) remain unchanged, the volume flows of liquid into and out of the reaction chambers are equal at all times. As much liquid per unit time is introduced to the reaction chamber from the first partial chamber as is removed from the second partial chamber.

A bioreactor preferably contains one single reaction chamber and precisely two partial chambers of the supply chamber. It is however, in principle, also possible to subdivide both chambers, in particular the supply chamber, into a plurality of partial chambers. For example, the supply chamber can be subdivided into four partial chambers, wherein the liquid flows substantially in pairs from the first and second partial chambers into the third and fourth partial chambers.

The inventions guarantees very good nutrient supply and waste removal for the producing system. A high production rate thereby results. The required bioreactor system is small, of relatively simple construction, and can therefore be manufactured economically.

Clearly, the circulation process can be interrupted during the biochemical reaction. An at least substantially continuous operation of the pump (during at least 80% of the reaction time) is, however, preferred.

In accordance with a preferred embodiment, the pumping direction and thereby the flow direction of the liquid is reversed during the biochemical reaction. Preferably the pumping direction is reversed a plurality of times during a biochemical reaction and, in accordance with an additional preferred embodiment, the respective volume pumped in one direction (up to the subsequent reversal of the pumping direction) is at least as large as the volume of the reaction chamber.

This type of operation can also be designated as "Modulation" of the flow and has the advantage that the formation of so-called secondary filter layers on the surface of the semi-permeable membrane is avoided. A secondary filter layer occurs when a concentration gradient of the material retained by the membrane is formed in front of the membrane wall during flow through the membrane in one direction. The filtering properties of the membrane are thereby negatively influenced. Avoidance of a secondary filter layer by modulation of the flow direction is known in the art from DE 3914956 A1.

This publication also discloses that it is advantageous to utilize an asymmetric semi-permeable membrane such that the actual filtration layer faces the reaction chamber. The present invention also preferably utilizes such an asymmetric membrane having the same orientation for separation of the reaction chamber and the supply chamber.

DE 3914956 A1 contains detailed description of the modulation procedure both with regard to the construction as well as the orientation of suitable membranes. This teaching can also be applied to the present invention taking into consideration its particular features. In this respect, the disclosure of the above mentioned publication is hereby incorporated by reference in the description of the present invention. A particular construction of an asymmetric membrane is the subject of WO 94/20603.

The invention is described in more detail below with reference to the embodiments represented in the figures.

Figure 1:
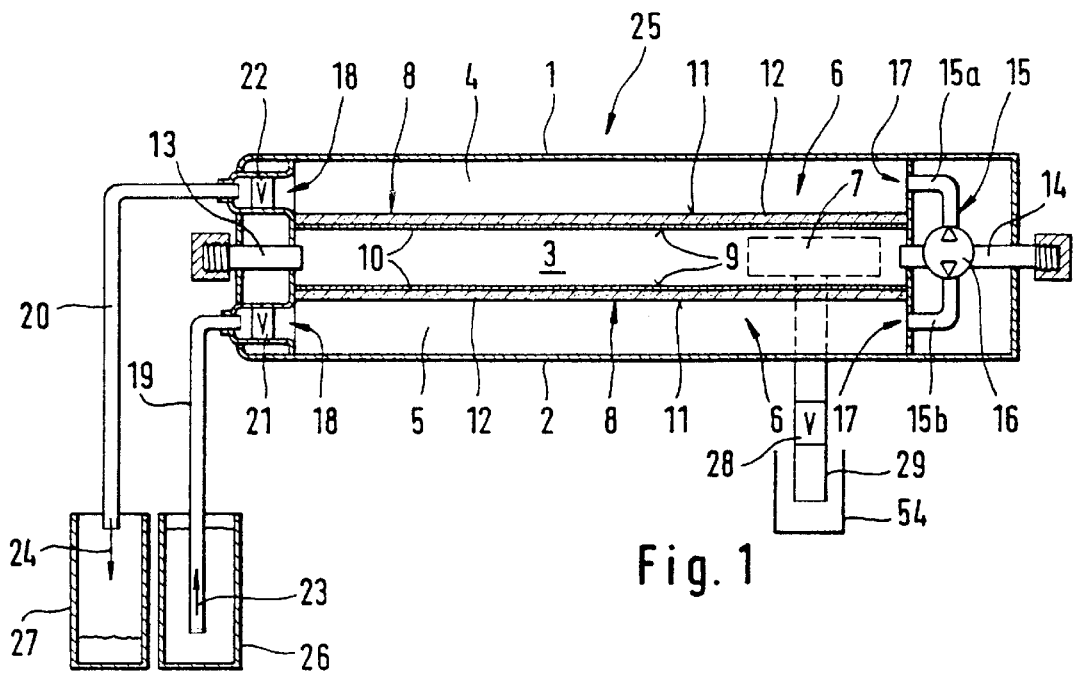
FIG. 1 shows a highly schematic cross section of a device in accordance with the invention.
Figure 3:
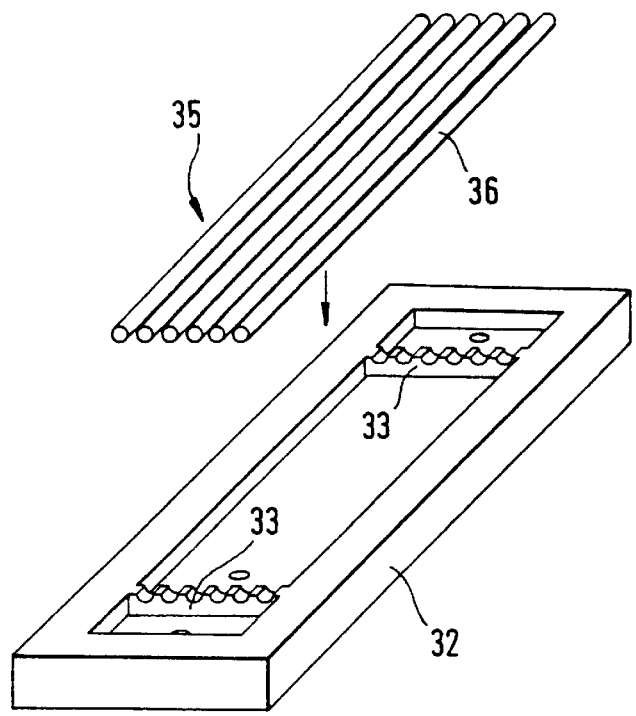
FIG. 3 shows an exploded view of components of a bioreactor module suitable for the invention.
Figure 4:
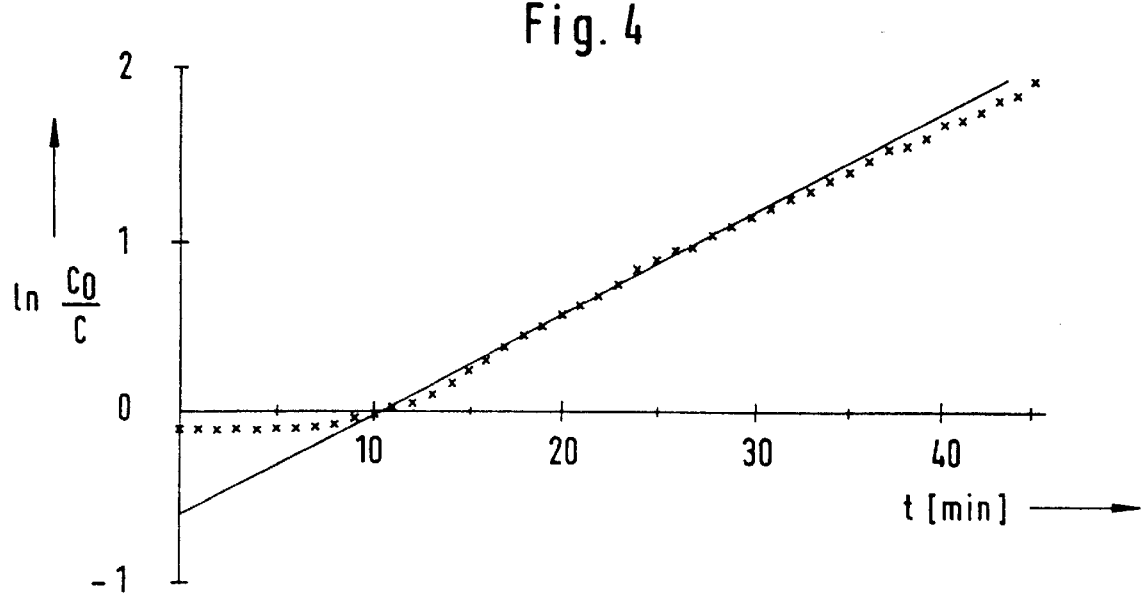
Figure 5:
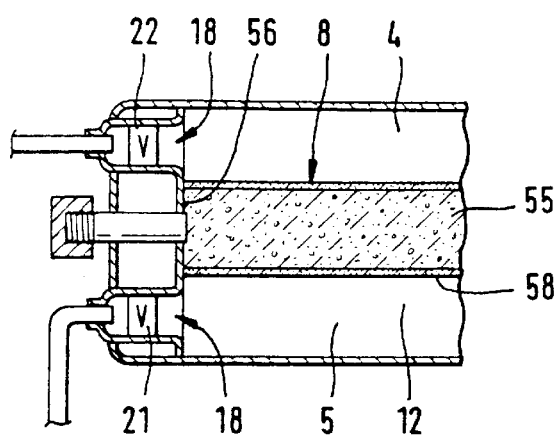
Figure 6:
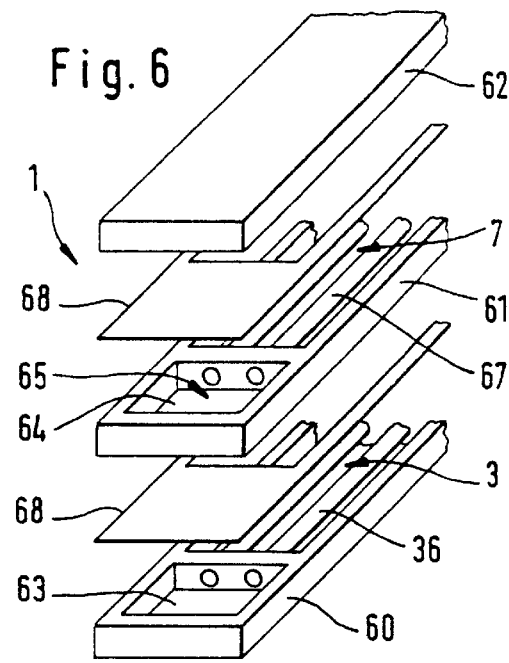
Figure 7:
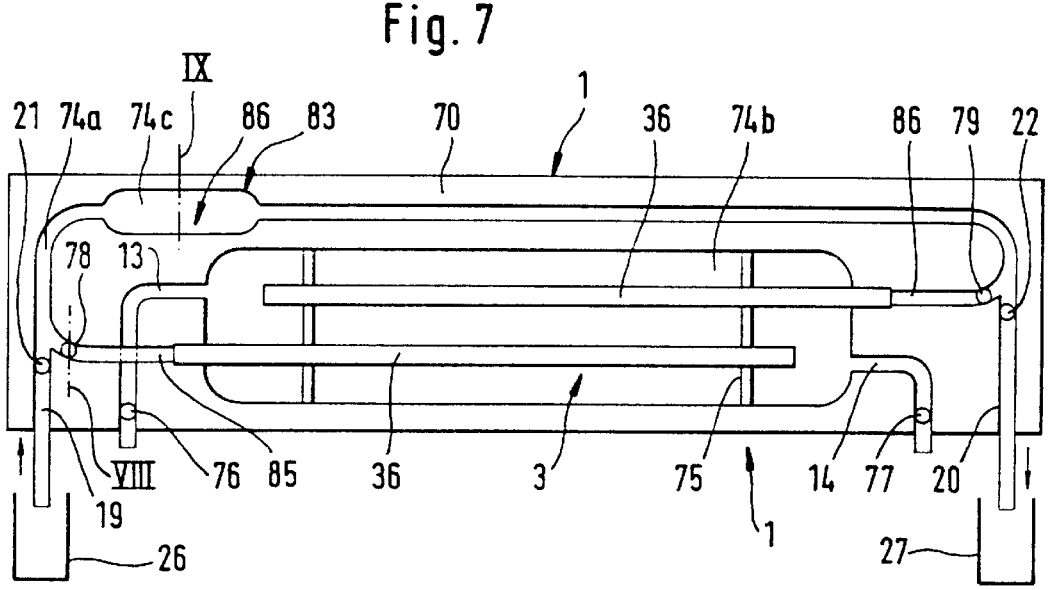
Figure 8:
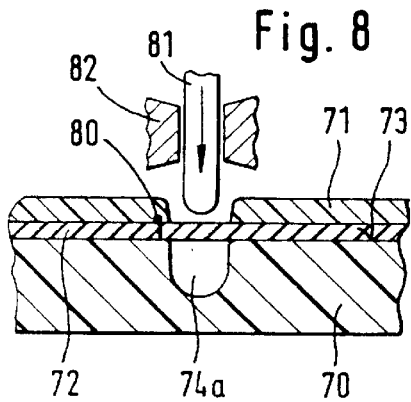
Figure 9:
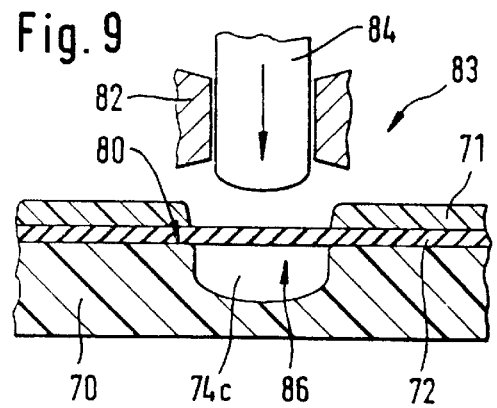

FIG. 4 shows a graphical representation of the response function during operation of a bioreactor system in accordance with the invention, FIG. 5 shows a portion of a cross section analogous to FIG. 1 of an alternative embodiment, FIG. 6 shows an exploded representation analogous to FIG. 3 of an alternative embodiment, FIG. 7 shows a view of a further alternative embodiment of a bioreaction module, FIG. 8 shows a detailed cut along line VIII of FIG. 7, FIG. 9 shows a detailed cut along line IX of FIG. 7.

The bioreactor 1 shown in FIG. 1 contains a reaction chamber 3 and two partial chambers 4, 5 of a supply chamber 6 within a housing 2. The two partial chambers 4, 5 are each connected to the reaction chamber 3 via a supply membrane 8. Each supply membrane 8 has a filtration layer 10 facing a first surface 9 and a support layer 12 facing a second surface 11. They are oriented in such a fashion that the first surface 9 (i.e. the filtration layer) faces the reaction chamber 3.

The two partial chambers 4, 5 of the supply chamber 6 are connected via a connection conduit 15 in which a pump 16 is disposed which can pump liquid through the conduit 15 in both flow directions. Each of the partial chambers 4, 5 of the supply chamber 6 are closed except for the permeability of membrane 8 and two connecting openings in each case, of which a first opening 17 effects a liquid connection to the connection conduit 15 and a second opening 18 a liquid connection to supply or removal conduits 19, 20 each of which can be closed-off by means of valves 21, 22. The connecting openings 17, 18 are, as shown, preferably disposed at opposite ends of the generally elongated partial chambers 4,5.

In the embodiment shown, the connection conduit 15 and the pump 16 are located within the housing 2 of the bioreactor 1. The valves 21, 22 are, as shown, also preferably integrated into the housing 2 of the bioreactor 1.

A biochemical reaction is carried out in the bioreactor system shown in FIG. 1 and designated in its totality as 25, in the following manner.

The reaction chamber 3 is filled, via connecting openings 13 and 14, with a liquid containing the producing system. The supply conduit 19 is connected to a container 26 containing a supply medium. The removal conduit leads into an initially empty container 27 for the eluate. The valves 21 and 22 are opened and, by means of the pump 16 or by means of an additional pump provided for in the supply conduit 19, liquid is initially transported into the second partial chamber 5 and subsequently into the first partial chamber 4 of the supply chamber 6 in the direction of arrows 23, 24 until both partial chambers as well as the conduits 19 and 20 are completely filled up to the valves 21, 22.

The valves 21 and 22 are then closed. When the pump 16 is set into operation with the valves 21, 22 closed, pressure is built up in the respective partial chamber, for example in partial chamber 4, when the pump 16 pumps into the upper section 15a of the connection conduit 15 in FIG. 1. The pressure causes fluid to flow out of the partial chamber 4 into the reaction chamber 3. Here again a pressure is built up by means of which the liquid flows further into the second partial chamber 5. From this location, the liquid flows, again under the action of the pump, into the lower section 15b of the connection conduit 16 and circulates further into the first partial chamber 4.

After, in this fashion, a liquid volume has been circulated which is at least as large as the volume of reaction chamber 3, the operation direction of the pump 16 is reversed to effect reverse flow. This procedure can be repeated a plurality of times during the entire reaction time.

After passage of the desired reaction time, the valves 21 and 22 are opened and a new pumping procedure is initiated in the direction of arrows 23, 24 to transport the supply medium, which then contains a substantial share of the desired product, into the eluate container 27. At the same time, fresh supply medium is introduced into the partial chambers 4, 5 of the supply chambers 6. After the contents of the supply chamber has been completely exchanged, a new biochemical reaction can be initiated.

In the method of operation described above, the desired product is extracted from the eluate of the supply medium. This requires the pores of the supply membrane. 8 to be sufficiently large that the product produced in the reaction chamber 3 passes into the supply chamber 6 during the described circulation procedure. This often requires (in dependence on the molecular weight of the desired product) a relatively coarse-pore membrane having a MW-cutoff of approximately 50,000 Dalton. Such a high MW-cutoff causes, however, not only the product and relatively low molecular components of the supply liquid (ATP, GTP and amino acids) to be pumped out of the reaction chamber 3, but also higher molecular and particularly valuable components of the producing system which should be saved.

For production of relatively high molecular products it is therefore more advantageous to directly extract ("harvest") the product from the reaction chamber. Towards this end, in accordance with an advantageous embodiment, an additional harvest membrane 7 is disposed in contact with the reaction chamber in such a fashion that liquid can be removed from the reaction chamber 3 via the harvest membrane to harvest the product produced by the producing system. In FIG. 1, the harvest membrane 7 is introduced in a wall defining the reaction chamber 3 and is connected to a container 54 via a conduit 29 which can be closed by a valve 28 for receiving the liquid removed from the reaction chamber 3 via the harvest membrane 7. The MW-cutoff of the harvest membrane 7 is larger than that of the supply membrane 8. Two differing operation modes are possible for harvesting the reaction chamber.

The valve 28 can be opened during operation of the pump 16. In this case, liquid is constantly removed from the reaction chamber 3 via the harvesting membrane 7 and passed through the conduit 29 due to the overpressure present in the reaction chamber 3. The amount can be regulated by setting the valve 28.

Generally preferred, however, is an operation mode which can be described as a batch harvest method. In this case harvesting is effected via the harvesting membrane 7 only after the biosynthesis procedure is ended and an increased product concentration is present in the reaction chamber 3. This is preferably carried out by closing the valve 22 and, via the pump 16, further forcing the supply liquid into the reaction chamber so that the liquid present in the reaction chamber 3 flows-off through the harvest membrane. Alternatively, a suitable liquid can be passed through one of the connecting openings 13 or 14 to press the liquid contained in the reaction chamber through the harvest membrane 7.

Harvesting with an additional harvest membrane has the advantage that the supply membrane 8 can be finer (e.g. have a transmission limit below 30,000 Dalton). In this manner, the loss of valuable substances from the reaction chamber 3 is minimized. On the other hand, the harvest membrane 7 can have a relatively high transmission limit (in excess of 70,000 Dalton). The associated losses of valuable constituents during harvesting are relatively low, in particular for the case of batch harvesting since, at the end of biosynthesis, a relatively high product concentration is achieved.

In the bioreactor system 25 of FIG. 1, the connection conduit 15 and the pump 16 are integrated within the housing of the bioreactor 2. The only required additional elements of the system are the conduits 19, 20 and the valves 21, 22. The pump 16 can, in principle, be an electrical micro-pump. In the embodiment shown in FIG. 1 having an integrated pump, it is however possibly advantageous to utilize a simpler type of pump. Possibilities include e.g. a reciprocating pump having a spring loaded piston, wherein the spring can be tensioned manually. The reciprocating pump should, in this case, have a stroke volume of at least the volume of the reaction chamber 3. In this case, it is helpful to use an additional electrical pump (not shown in the figure) in the conduit 19 for filling and emptying the supply chamber 6.

Figure 2:
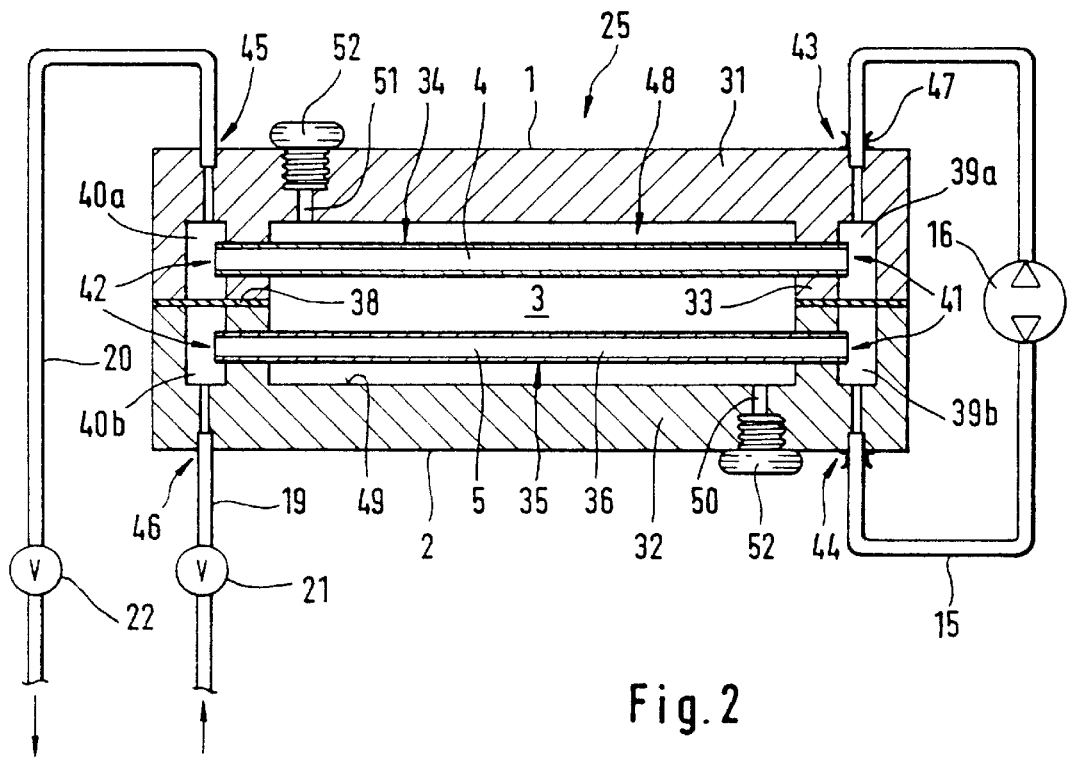
FIG. 2 shows a schematic cross section of an alternative embodiment of a device in accordance with the invention.

In the embodiments shown in FIGS. 2 and 3, corresponding components are designated with the same reference symbols as in FIG. 1, even if they are configured somewhat differently in detail. Whereas a flat membrane (for example a membrane filter layer 10 disposed on a support comprising sintered material 12) is utilized in FIG. 1, the bioreactor 1 shown in FIG. 2 is equipped with hollow fiber membranes designated below as "capillaries".

In this embodiment, housing 2 of bioreactor 1 comprises two halves 31 and 32, wherein each of the halves has end walls 33 into which a set 34 and 35 respectively of parallel capillaries 36, extending in a common plane, are introduced in a sealed manner. The two halves 31, 32 are held together using means not shown (for example clamps or screws), wherein the flat seal 38 is disposed between them. The two halves can also be connected in a sealed and secured fashion by means of gluing or welding.

In the design shown a collection chamber 39a, 39b, 40a, 40b is formed at both ends of each set 34, 35 of capillaries 36 which is connected to one end of the inner volume of the capillaries of one set and to a connection opening 43, 44, 45, 46, but which is otherwise sealed. Thus, in each case, a first end 41 of the capillaries 36 is connected, via the corresponding collection chamber 39a and 39b respectively, to a connection opening 43 and 44 respectively for the connection conduit. A second end 42 is connected, via an associated collection volume 40a and 40b respectively, to a connection opening 45 and 46 respectively for a supply conduit 19 or a removal conduit 20. The collection chambers 39a, 39b, 40a, 40b thereby each constitute a common conduit connection for a set of capillaries 34 or 35 in combination with the corresponding associated connection openings 43, 44; 45, 46. The inner spaces of the capillaries of the capillary set 34 form, together with the collection chambers 39a, 40a, the first partial chamber 4 of the supply chamber 6. The inner spaces of the capillary set 35 form, together with the collection chambers 39b, 40b, the second partial chamber 5 of the supply chamber 6.

In this embodiment, the outer chamber 48 between the capillaries 36 and the wall 49 of the housing 2 constitutes the reaction chamber 3. This volume can be filled, without the formation of bubbles, with the liquid containing the producing system via an inlet opening 50 and a vent opening 51 disposed diametrically across therefrom. The openings 50, 51 are closed during the biochemical reaction by means of e.g. a plug 52. The capillaries 36 of both capillary sets 34, 35 extend substantially parallel to each other through the reaction chamber 3.

In the embodiment shown here the connection conduit 15, in which a pump 16 is integrated, extends outside of the bioreactor 1 and is connected by means of schematically represented couplings 47. Thus, in this case the bioreactor system 25 consists of the bioreactor 1, the conduits 15, 19, 20, the valves 21, 22, and the pump 16.

Use of capillaries instead of flat membranes is preferred, since a large membrane surface can thereby be provided in a simple and economical fashion. As in FIG. 1, the membranes of the capillaries 36 are preferably formed asymmetrically with respect to the filter layer facing the reaction chamber 3 (see DE 3114956 A1).

Performing of a biochemical reaction using the bioreactor system in accordance with FIGS. 2 and 3 is analogous to that of FIG. 1.

FIG. 4 shows the response function of a bioreactor in accordance with FIGS. 2 and 3. The change in concentration of an easily detectable low molecular weight substance contained in the reaction chamber 3 at the beginning of the experiment is tracked through time during operation of the bioreactor. This "model reaction" was started after 10 minutes and run for an additional 35 minutes, wherein the pump 16 was in constant operation and the pumping direction was reversed every 60 seconds.

FIG. 4 shows the change in concentration observed in the reaction chamber. The ordinate plots the natural logarithm of the initial concentration divided by the instantaneous concentration $\ln C_O/C$ versus time in minutes. A linear dependence is observed. This corresponds to an exponential decrease in concentration as is characteristic for a conventional flow-through reactor having a continuously flowed through membrane. This agreement in the response function illustrates that the supply conditions for the producing system in the present invention are as good as those of the flow-through reactor. The volume relationship, the amount of the producing system (in particular mRNA) which is required, and the concentration of the product in the eluate are however substantially better.

The invention thereby allows a very effective overall processing of biochemical reactions in a relatively simple manner. In addition the following specific advantages are obtained:

The ratio of the volume of the reaction chamber to the volume of the supply chamber ("phase ratio") can be chosen over a wide range. In particular, one can operate with a small reaction chamber volume. In combination with modulation of the pumping process, the formation of secondary filter layers and the associated depletion of the biologically active macromolecules in the reaction chamber can be avoided.

The flat shape of the bioreactor in accordance with the invention simplifies filling of the reaction chamber and facilitates a simple and effective venting.

Deposits are avoided since the liquid flows smoothly through the supply chamber along its longitudinal extension and since, in particular, the liquid passes along the entire capillaries. Also a complete transfer of the entire reaction product for further processing is possible without rinsing and associated thinning effects.

The module body can be produced from two identical units in which the capillaries are disposed in a plane. The partial chambers 4 and 5 formed by the inner space of the capillaries can be easily connected to the required connectors for supply and removal.

In the embodiment shown in FIG. 5, the reaction chamber 3 is filled with a porous body 55 whose pores contain the components of the producing system. The porous body can, e.g. consist essentially of a glass frit or porous ceramic material.

As in FIG. 1, the producing system can be fed into the porous body 55 through its end faces 56 via the connecting openings 13 and 14. However, at least some of the components of the producing system are preferably pre-packed into the porous body 55, i.e. these components are introduced into the pores of the solid body 55 during manufacture of the bioreactor 1 and delivered to the user along with the bioreactor which already contains a large fraction of the components of the producing system. In this case storage in a porous body is advantageous. It is however, in principle, also possible to produce a bioreactor in accordance with other embodiments of the invention in such a form that the reaction chamber 3 contains a part of the components of the producing system pre-packed (for example in the form of a freeze-dried layer on its wall or as a tablet).

In the embodiment of FIG. 5, the supply membrane 8 is preferably located at the outer surface of the porous body. For example, a fine porous membrane layer 58 can be evaporated as an outer jacket onto the porous body 55. In recent times, methods have also become available for the manufacture of a single-unit porous body 55 having outer surface pores which are substantially finer than the internal ones so that the fine pore outer surface forms a semipermeable membrane layer 58.

FIG. 6 illustrates the manner in which an additional harvest membrane can be provided for in a capillary reactor similar to FIGS. 2 and 3. In this case, the housing of the bioreactor 1 consists essentially of three molded members 60, 61 and 62 each having a collection chamber, wherein only the collection chamber 63 and 64 of the molded members 60 and 61 can be seen in the figure. The collection chambers are each connected in a similar manner as in FIGS. 2 and 3 on one side with connection openings (not shown here) and on the other side with the inner spaces of capillaries 36, wherein the capillaries 36 in the outer molded members 60 and 62 constitute the supply membrane 8, and the harvest membrane 7 is formed by the capillaries 67 in the middle molded member 61. The collection chambers 63 and 64 as well as the collection chamber of the molded member 62 (not shown) are separated from each other within the bioreactor module formed by the molded members 60, 61 and 62 by seals 68. The collection chamber 64 forms, together with a connection opening not shown in FIG. 6, a common conduit connection 65 for the capillaries 67 of the harvest membrane 7 to remove the liquid during harvesting of the product. The capillaries 36 and 67, which constitute the supply membrane 8 and the harvest membrane 7, are located in a common reaction chamber 3 which is formed by the outer volume between the capillaries 36 and the surrounding housing wall.

FIGS. 7 through 9 show constructive solutions for problems which are particularly suitable for a micro-membrane-reactor in accordance with the above described invention but which also have independent significance for other bioreactors of very small size.

The bioreactor 1 shown in FIGS. 7 through 9 consists essentially of a profiled molded member 70 made from plastic, a cover member 71 covering same over a large surface, and a thin elastic foil 72 disposed between the profiled molded member 70 and the cover member 71. The foil 72 should be made from a highly elastic inert material such as silicon rubber.

Recesses, indicated in their totality as 74, are located in the cover surface 73 of the generally cuboid shaped molded member 70. The conduits required for the bioreactor are formed by narrow grooved recesses 74a which can have a cross sectional area of e.g. 0.5 to 1 mm². The reaction volume 3 is formed by a larger trough-shaped recess 74b in which hollow fibers (capillaries) 36 extend, fixed by brace rods 75.

Similar to the bioreactor of FIG. 1, the bioreactor of FIG. 7 has valves to selectively close the conduits. Shown are valves 21 and 22 for closing the supply conduit 19 and the removal conduit 20 respectively and valves 76, 77 for closing the connection openings 13 and 14 of the reaction chamber 3. Additional valves 78, 79 are disposed in each of the conduit connections of the capillaries 36 to allow a pumping action which will be described below.

FIG. 8 illustrates functioning of the valves 21, 22 and 76 through 79. The foil 72 is spanned between the cover member 71 and the profiled molded member 70 in such a fashion that it covers the edge 80 of the groove 74a in a sealing manner. A valve operation pin 81 is movable vertically in a guide 42 above the foil in such a fashion that, in a closed position of the valve, it pushes the foil into the groove and, in the open position shown, releases the foil so that it is stretched over the groove. Operation of the pin 81 can be effected in conventional manner, e. g. electromagnetically or piezoelectrically.

The bioreactor 1 shown in FIG. 7 has an additional recess 74c which is part of a miniature pump 83. The recess 74c is closed at its upper side by an elastic foil 72 sealingly covering its edge 80. The conduits connecting to the recess 74c can each be closed by valves 20, 21, 78, 79. The chamber of the recess 74c forms, together with the conduit portions connected thereto, up to the valves 20, 21, 78, 79, a pumping chamber volume 86.

A pump operation pin 84 guided by a guide 82 is disposed above the foil which, in a first position, pushes the foil into the pump chamber volume 74c so that it reduces the volume of same and, in a second position, releases the foils 72 so that it is stretched over the pumping chamber volume 74c.

In the example shown, the pump 83 serves both for suctioning and removing the supply liquid via the supply conduit 19 and the removal conduit 20 which can be closed by the valves 21 and 22 as well as for circulation during biosynthesis via the connection conduits 85 and 86 of the capillaries 36. The function is illustrated using as an example the suctioning of the supply liquid out of the container 26.

The valve 21 is initially opened and the pump operation pin 84 is moved down to reduce the pump chamber volume 86. The suction opening of the supply conduit 19 is then submerged into the supply liquid located in the container 26 and suction action is effected by lifting the pump operation pin 84 with resulting increase of the pump chamber volume 86. The valve 21 is closed and the valve 22 opened. The liquid is pushed in the direction of valve 22 by lowering the pump operation pin 84. After closing the valve 22 and opening the valve 21, a new suctioning process follows with the subsequent lifting of the pump operation pin 84. Cyclic repetition of these steps allows pumping of any desired amount of liquid through the conduit in which the pump 83 is located. Circulation through the capillaries 36 is effected analogously using valves 78 and 79, while the valves 21 and 22 are closed.

Thus, the design features illustrated in FIGS. 7 through 9 allow a simple and reliable overall operation of a compact bioreactor.

We claim:

1. A method for carrying out a biochemical reaction by means of a bioreactor comprising a housing and, inside said housing, (A) a reaction chamber comprising a producing system; and (B) a supply chamber containing a liquid, which liquid serves as a supply medium for said producing system, wherein said supply chamber is subdivided into first and second partial chambers, with said first and second partial chambers being
  (a) interconnected via a connection conduit, and
  (b) independently separated from said reaction chamber by a semi-permeable supply membrane, which method comprising, during the biochemical reaction, three simultaneous steps of (i) passing said liquid out of the first partial chamber into said reaction chamber;

(ii) passing said liquid from said reaction chamber into the second partial chamber; and (iii) passing said liquid out of the second partial chamber via the connection conduit into the first partial chamber;

in order to circulate said liquid in a flow direction of from the first partial chamber through said reaction chamber into the second partial chamber.

2. The method of claim 1, wherein the biochemical reaction is for a cell-free polypeptide biosynthesis.

3. The method of claim 1, wherein said liquid is passed between said first and second partial chambers by the action of a pump.

4. The method of claim 1, wherein the volumes of liquid in the reaction chamber and the first and second partial chambers remain constant during circulation with the volume flow of said liquid into said reaction chamber being equal to the volume flow of said liquid out of said reaction chamber.

5. A method for obtaining a product of a biochemical reaction, comprising the following steps:

I. conducting the method of claim 1, and

II. extracting a product of the biochemical reaction from said liquid.

6. A method for obtaining a product of a biochemical reaction, comprising the following steps:

I. conducting the method of claim 1, wherein said reaction chamber further comprises a semi-permeable harvesting membrane, and II. extracting a product produced by the producing system via said semi-permeable harvesting membrane.

7. The method of claim 1, further comprising, during the biochemical reaction, reversing the flow direction of said liquid at least once by simultaneously (i) passing said liquid out of the second partial chamber into said reaction chamber;

(ii) passing said liquid from said reaction chamber into the first partial chamber; and (iii) passing said liquid out of the first partial chamber via the connection conduit into the second partial chamber.

8. The method of claim 7, wherein the flow direction is reversed a plurality of times during the biochemical reaction.

9. The method of claim 7, wherein said reaction chamber has a volume and the volume of said liquid passed in one direction, before the flow direction is reversed, is at least as large as the volume of said reaction chamber.

10. The method of claim 1, wherein said producing system comprises at least one enzyme for the biochemical reaction.

11. The method of claim 2, wherein said producing system comprises a messenger RNA which encodes said polypeptide, ribosomes, tRNA, amino acids, ATP and GTP.

* * * * *